US00PP15600P2

(12) United States Plant Patent
Olesen et al.

(10) Patent No.: US PP15,600 P2
(45) Date of Patent: Mar. 1, 2005

(54) ROSE PLANT NAMED 'POULPM001'

(50) Latin Name: *Rosa hybrida*
Varietal Denomination: POULpm001

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 38 days.

(21) Appl. No.: 10/738,151

(22) Filed: Dec. 16, 2003

(51) Int. Cl.[7] ..... A01H 5/00
(52) U.S. Cl. ..... Plt./137
(58) Field of Search ..... Plt./137, 133, 148

*Primary Examiner*—Anne Marie Grunberg
*Assistant Examiner*—June Hwu

(57) ABSTRACT

A new garden rose plant of the hybrid tea class which has abundant, light pink flowers and attractive foliage. This new and distinct variety has shown to be uniform and stable in the resulting generations from asexual propagation.

2 Drawing Sheets

Botanical classification: *Rosa hybrida.*
Variety denomination: 'POULpm001'.

SUMMARY OF THE INVENTION

The present invention constitutes a new and distinct variety of garden rose plant which originated from a controlled crossing between the unnamed female parent plant and the male parent 'POULdrik', described and illustrated in U.S. Plant Pat. No. 12,557 issued Apr. 23, 2002. The two parents were crossed during the summer of 1991 and the resulting seeds were planted in a controlled environment in Fredensborg, Denmark. The new variety is named 'POULpm001'.

The new variety may be distinguished from its seed parent, by the following combination of characteristics:

1. While the seed parent has dark pink flowers. 'POULpm001' is light pink.
2. While the seed parent has a short growth height, less than 60 cm in height, 'POULpm001' is 60 to 100 cm in height.
3. While the seed parent develops single flower buds per flowering stem, 'POULpm001' will develop 1 to 3 flower buds per flowering stem.

The new variety may be distinguished from its male pollen parent, 'POULdrik', by the following combination of characteristics:

1. While the pollen parent 'POULdrik' has a petal color, as the sepals unfold, of Red Group 46D, the same of 'POULpm001' is Yellow-Green Group 145C.
2. While the pollen parent 'POULdrik' has a sepal size of 15 mm long and 10 mm wide the same of 'POULpm001' are larger, measuring 30 mm long and 12 mm wide.
3. While the pollen parent 'POULdrik' has a general tonality of Red Group 64D. 'POULpm001' has a general tonality of Red Group 36A to 36D.

The objective of the hybridization of this rose variety was to create a new and distinct variety for garden use with unique qualities, such as:

1. Uniform and abundant light pink flowers;
2. Vigorous, but compact growth when propagated both as a budded rose and on its own roots;

4. Good branching habit;
3. Disease resistance.

This combination of qualities is not present in previously available commercial cultivars of this type, known to the inventors, and distinguish 'POULpm001' from all other varieties of which we are aware.

As part of their rose development program, L. Pernille Olesen and Mogens N. Olesen germinated the seeds from the aforementioned hybridization during winter of 1991 and conducted evaluations on the resulting seedlings in a controlled environment in Fredensborg, Denmark.

'POULpm001' was selected in the spring 1992 by the inventors as a single plant from the progeny of the aforementioned hybridization.

Asexual reproduction of 'POULpm001' by traditional budding and rooted cuttings was first done by L. Pernille and Mogens N. Olesen in their nursery in Fredensborg, Denmark in July, 1992. This initial and other subsequent asexual propagations conducted in controlled environments have demonstrated that the characteristics of 'POULpm001' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULpm001'.

Specifically illustrated in SHEET 1:

FIG. 1.2; Flower bud closed, flower bud as sepals unfold, and partially open;

Specifically illustrated in SHEET 2:

FIG. 2.2; Sepals, receptacle, and peduncle;

FIG. 2.3; Mature leaves and juvenile leaves;

FIG. 2.4; Bare stem exhibiting thorns.

DETAILED DESCRIPTION OF THE VARIETY

Figures 1, 2:
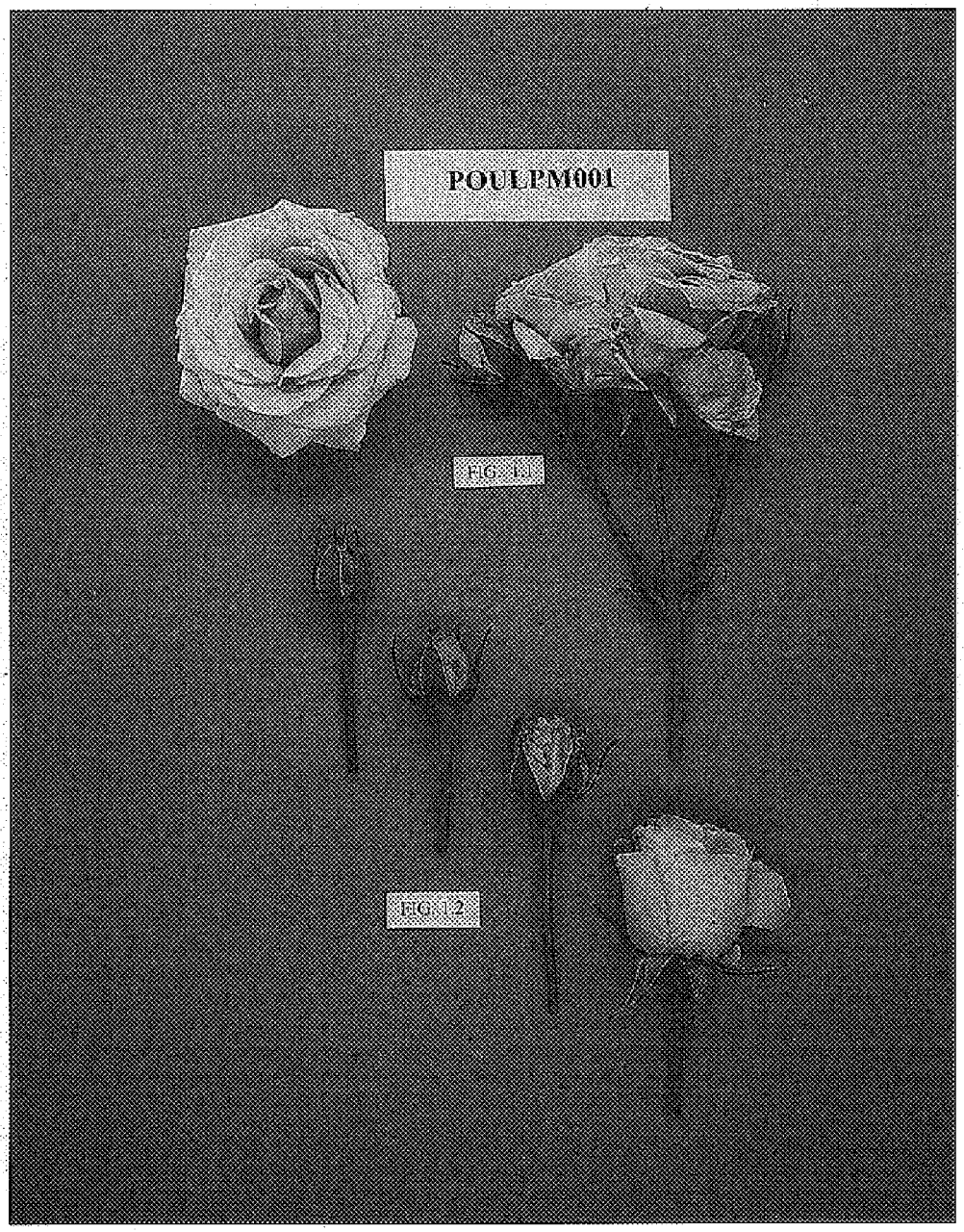
FIG. 1.1; Open flower, stem showing open flower, branching, and the attachment of leaves, buds, and peduncles.
FIG. 2.1; Flower petals, detached.

The following is a description of 'POULpm001', as observed in its growth in a field nursery in Jackson County, Oreg. Observed plants are 3 years of age, and were grown on *Rosa multiflora* root stock. Color references are made using The Royal Horticultural Society, (London, England) Colour Chart, 1995, except where common terms of color are used.

For a comparison, several physical characteristics of the rose variety 'POULasor', a rose variety from the same inventors described and illustrated in U.S. Plant patent application Ser. No. 10/339,871 dated Jan. 10, 2003 are compared to 'POULpm001' in Chart 1.

CHART 1

| | 'POULpm001' | 'POULasor' |
|---|---|---|
| Color of outer flower petals after opening | Upper side: White Group 155D to Orange-White Group 159D. | Red Group 55D |
| Petalage | 35 to 40 petals | 25 to 27 petals |
| Flower diameter | 75 to 85 mm | 55 mm |

Parents:

*Female seed parent.*—Unnamed plant.

*Male pollen parent.*—'POULdrik'.

FLOWER AND FLOWER BUD

Blooming habit: Recurrent.

Flower bud:

*Size.*—Upon opening, 30 mm in length from base of receptacle to end of bud.

*Bud form.*—Broad Based ovoid.

*Bud color.*—As sepals unfold, petals are Yellow-Green Group 145C with intonations of Orange Group 29C and Red Group 39A. At ¼ opening petals are Red Group 39C.

*Sepals.*—Upper Surface: Color: Yellow-Green Group 145A to 146A. Surface: Strongly pubescent. Lower Surface: Color: Yellow-Green Group 144A to 144B. Sepal Shape: Sepal apex is cirrose. Base is flat at union with receptacle. Sepal Margin: Margins have weak foliaceous appendages on three of the five sepals. Size: 30 mm (l)×12 mm (w).

*Receptacle.*—Surface: Glaucous. Shape: Funnel shaped. Size: 8 mm (h)×11 mm (w). Color: Yellow-Green Group 144A. Anthocyanin: None observed.

*Peduncle.*—Surface: Abundance of stipitate glands which exhibit a strong fragrance. Length: 60 to 65 mm. Diameter: 4 mm. Color: Yellow-Green Group 144C. Anthocyanin: Greyed-Red Group 180B. Strength: Strong.

*Borne.*—In small clusters. Typically 3 flower buds per stem.

Flower bloom:

*Fragrance.*—Moderate rose scent.

*Duration.*—The blooms have a duration on the plant of approximately 10 days. Afterwards petals fall cleanly away from plant.

*Size.*—Average range of flower diameter is 75 to 80 mm when open.

*Form.*—General shape is a deep cup with a high center. Outer petals slightly overlap.

*Shape of flower when viewed from the side.*—Upon opening, upper part: Flat. Upon opening, lower part: Concave. Open flower, upper part: Flattened convex. Open flower, lower part: Concave.

*Petalage.*—On average 35 to 40 petals under normal conditions with 16 petaloids.

Color:

*Upon opening, petals.*—Outermost petals: Outer side: Red Group 39D at basal to middle zone. White Group 155D to Red Group 36D at marginal to middle zone. Inner Side: White Group 155D to Orange-White Group 159D. Innermost petals: Outer side: Red Group 39D at basal to middle zone. White Group 155D to Red Group 36D at marginal to middle zone. Inner Side: White Group 155D to Orange-White Group 159D.

*Upon opening, basal petal spots.*—Upper and lower surfaces are Yellow Group 2D.

*After opening, petals.*—Outermost petals: Outer side: Red Group 39D at basal to middle zone. White Group 155D to Red Group 36D at marginal to middle zone. Inner Side: White Group 155D to Orange-White Group 159D. Innermost petals: Outer side: Red Group 39D at basal to middle zone. White Group 155D to Red Group 36D at marginal to middle zone. Inner Side: White Group 155D to Orange-White Group 159D.

*After opening, basal petal spots.*—Upper and lower surfaces are Yellow Group 2D.

General tonality: On an open flower overall color is Red group 36A to 36D. No change in the general tonality at the end of the 10th day.

Petals:

*Petal reflex.*—Inner petals reflex somewhat. Outer petals reflex strongly.

*Margin.*—Entire and uniform. Medium undulations of margin.

*Shape.*—Apex is Round. The base shape is generally acute but somewhat rounded at the petal base.

*Size.*—48 mm (l)×48 mm (w).

*Texture.*—Smooth.

*Thickness.*—Average.

*Arrangement.*—Not Formal.

Petaloids:

*Quantity.*—15 to 20.

*Color.*—Red Group 39D.

*Size.*—28 mm (l)×25 mm (w).

Reproductive organs:

*Pistils.*—Length: 10 mm long. Quantity: 135 (actual count).

*Pollen.*—None observed.

*Anthers.*—Size: 3 mm long. Color: Greyed-Orange Group 163B. Quantity: 138 (actual count).

*Filaments.*—Color: Yellow Group 3A. Length: 8 mm.

*Stigmas.*—Superior relative to the height and length of the filaments and anthers. Color: Greyed-Yellow Group 160C.

*Styles.*—Color: Yellow-Green Group 150D. Other Intonations: Red Group 48B.

*Hips.*—None Observed in the field nursery in Jackson County Oreg.

PLANT

Plant growth: Moderate, upright to bushy. When grown as a budded field grown plant on *Rosa multiflora* understock, the height of the plant is 80 to 100 cm and the average width is 50 to 70 cm.

Stems:

*Color.*—Young wood: Yellow-Green Group 145A with intonations of Greyed-Red 178B to 178C. Older wood: Yellow-Green Group 146B.

*Surface texture.*—Young wood: Smooth. Older wood: Smooth.

Thorns:

*Incidence.*—6 thorns per 10 cm of stem.

*Size.*—Average length: 8 mm.

*Color.*—Mature thorns are Greyed-Yellow Group 162A to Greyed-Orange 166C. Juvenile thorns are Greyed-Yellow Group 160B to Yellow-Green Group 145C.

*Shape.*—Concave.

Plant foliage: Normal number of leaflets on leaves in middle of the stem: 7 leaflets.

*Compound leaf size.*—200 mm (l)×100 mm (w).

*Color.*—Mature Foliage: Upper surface is Yellow-Green Group 147A. Lower surface is Yellow-Green Group 147B. Juvenile foliage: Upper surface is Yellow-Green Group 146A. Lower Leaf Surface is Greyed-Red Group 183A with intonations of Yellow-Green Group 144B. Anthocyanin: Location: Juvenile leaves. Color: Greyed-Red Group 183A.

Plant leaves and leaflets:

*Stipules.*—Size: 30 mm in length. Color: Green Group 137A. Margins: Finely serrated with medium stipitate glands.

*Petiole.*—Length: 40 mm. Color: Yellow-Green Group 144B. Anthocyanin: Light Greyed-Red Group 180A. Underneath: Prickles and stipitate glands observed.

*Rachis.*—Length: 90 mm. Color: Yellow-Green Group 144B. Anthocyanin: Very light intonations of Greyed-Red Group 180A. Underneath: Prickles and stipitate glands present.

*Leaflet.*—Size: 62 mm (l)×52 mm (w). Edge: Serrated. Shape: Broadly ovate to round. Base is rounded. Apex is cuspidate. Texture: Smooth. Arrangement: Odd pinnate. Venation: Reticulate. Glossiness: Glossy. Thickness: Thick.

Disease resistance: Above average resistance to mildew, rust, black spot, and Botrytis under normal growing conditions in Jackson County, Oreg.

Cold hardiness: The variety 'POULpm001' has been found to be cold tolerant to USDA Cold Hardiness Zone 6.

It is claimed:

1. A new and distinct variety of rose plant of the hybrid tea class, substantially as herein illustrated and described as a distinct and novel rose variety due to its abundant light pink, disease resistance, and extended period of bloom.

* * * * *

POULPM001

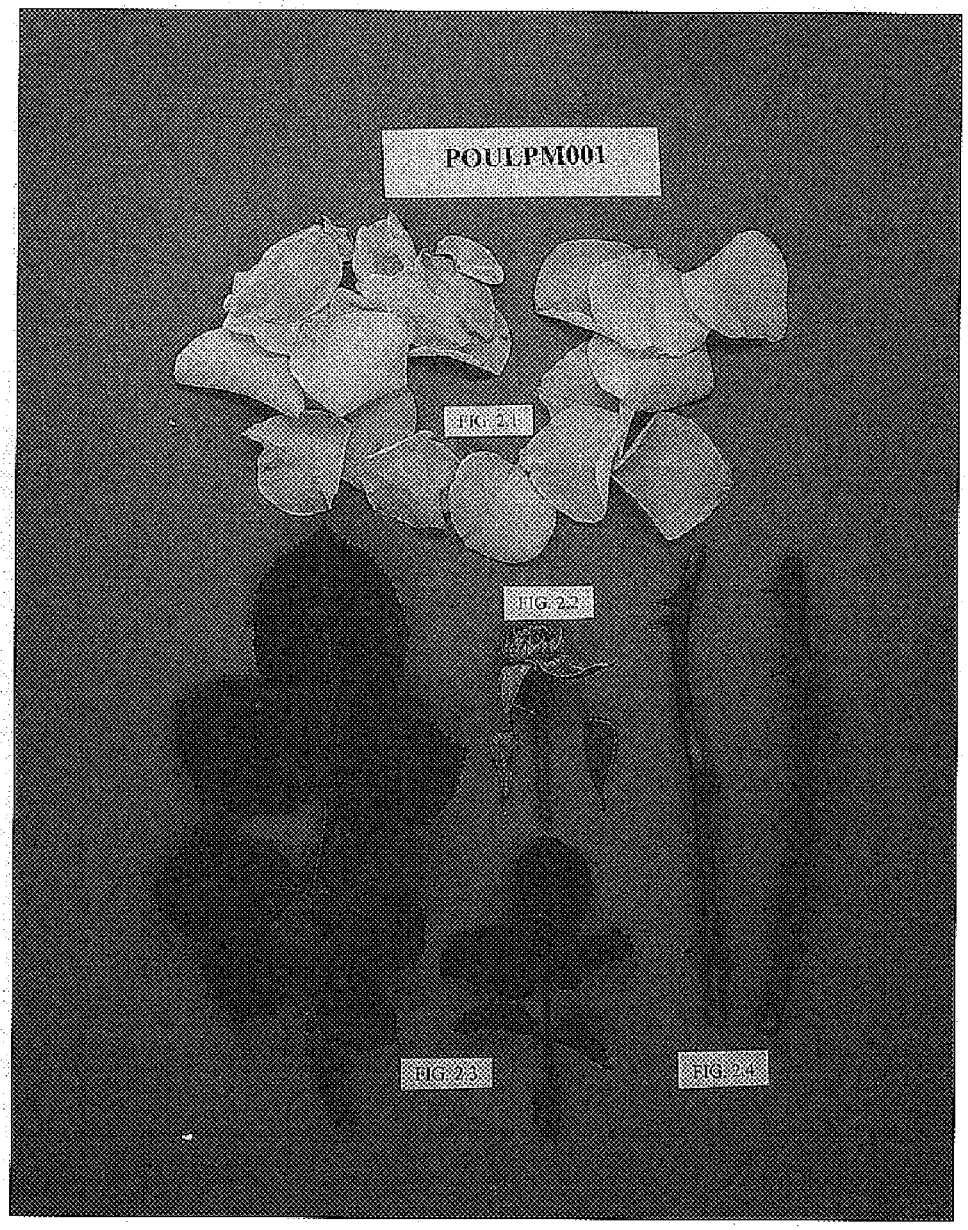
POULPM001
FIG. 2.1
FIG. 2.2
FIG. 2.3
FIG. 2.4